(12) United States Patent
Kappus et al.

(10) Patent No.: US 10,213,221 B2
(45) Date of Patent: Feb. 26, 2019

(54) SURGICAL INSTRUMENTS INCLUDING CAM SURFACES

(71) Applicant: COVIDIEN LP, Mansfield, MA (US)

(72) Inventors: John J. Kappus, Denver, CO (US); David N. Heard, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 217 days.

(21) Appl. No.: 15/230,046

(22) Filed: Aug. 5, 2016

(65) Prior Publication Data
US 2017/0119417 A1    May 4, 2017

Related U.S. Application Data

(60) Provisional application No. 62/247,279, filed on Oct. 28, 2015.

(51) Int. Cl.
| | |
|---|---|
| A61B 17/29 | (2006.01) |
| A61B 18/14 | (2006.01) |
| A61B 17/00 | (2006.01) |
| A61B 17/28 | (2006.01) |

(52) U.S. Cl.
CPC ........ *A61B 17/29* (2013.01); *A61B 17/00234* (2013.01); *A61B 17/2812* (2013.01); *A61B 17/2909* (2013.01); *A61B 18/1445* (2013.01); *A61B 2017/00367* (2013.01);
(Continued)

(58) Field of Classification Search
CPC .............. A61B 17/29; A61B 17/00234; A61B 17/2812; A61B 17/2909; A61B 2017/00367; A61B 2017/2913
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |

(Continued)

FOREIGN PATENT DOCUMENTS

| | | |
|---|---|---|
| CN | 201299462 | 9/2009 |
| DE | 2415263 A1 | 10/1975 |

(Continued)

OTHER PUBLICATIONS

Heniford et al. "Initial Research and Clinical Results with an Electrothermal Bipolar Vessel Sealer" Oct. 1999. (1 page).
(Continued)

*Primary Examiner* — Katrina Stransky

(57) ABSTRACT

A surgical instrument includes a housing, a handle, an elongated shaft, an end effector assembly, a drive assembly, and an extension depending from the handle. The extension includes a proximal surface having a first proximal cam portion defining a first angle with respect to the longitudinal axis and a second proximal cam portion defining a second angle with respect to the longitudinal axis. Initial actuation of the handle from a non-actuated position causes the first proximal cam portion to contact the first portion of the drive assembly causing a first movement of the at least one jaw member, and a subsequent actuation of the handle causes the second proximal cam portion to contact the first portion of the drive assembly causing a second movement of the at least one jaw member.

16 Claims, 9 Drawing Sheets

(52) U.S. Cl.
CPC .......... *A61B 2017/2913* (2013.01); *A61B 2017/2915* (2013.01); *A61B 2018/1455* (2013.01)

(56) References Cited

U.S. PATENT DOCUMENTS

| | | | |
|---|---|---|---|
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| 5,527,313 A * | 6/1996 | Scott | A61B 17/2909 606/41 |
| 5,582,615 A | 12/1996 | Foshee et al. | |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| D670,808 S | 11/2012 | Moua et al. | |
| D680,220 S | 4/2013 | Rachlin | |
| 9,084,608 B2 | 7/2015 | Larson et al. | |
| 9,211,657 B2 | 12/2015 | Ackley et al. | |
| 2005/0209596 A1 | 9/2005 | Daniels et al. | |
| 2010/0004677 A1 | 1/2010 | Brostoff et al. | |
| 2012/0316601 A1 | 12/2012 | Twomey | |
| 2014/0135805 A1 * | 5/2014 | Windgassen | A61B 17/295 606/170 |
| 2014/0221995 A1 | 8/2014 | Guerra et al. | |
| 2014/0221999 A1 | 8/2014 | Cunningham et al. | |
| 2014/0228842 A1 | 8/2014 | Dycus et al. | |
| 2014/0230243 A1 | 8/2014 | Roy et al. | |
| 2014/0236149 A1 | 8/2014 | Kharin et al. | |
| 2014/0243811 A1 | 8/2014 | Reschke et al. | |
| 2014/0243824 A1 | 8/2014 | Gilbert | |
| 2014/0249528 A1 | 9/2014 | Hixson et al. | |
| 2014/0250686 A1 | 9/2014 | Hempstead et al. | |
| 2014/0257274 A1 * | 9/2014 | McCullough, Jr. | A61B 18/1445 606/40 |
| 2014/0257283 A1 | 9/2014 | Johnson et al. | |
| 2014/0257284 A1 | 9/2014 | Artale | |
| 2014/0257285 A1 | 9/2014 | Moua | |
| 2014/0276803 A1 | 9/2014 | Hart | |
| 2014/0284313 A1 | 9/2014 | Allen, IV et al. | |
| 2014/0288549 A1 | 9/2014 | McKenna et al. | |
| 2014/0288553 A1 | 9/2014 | Johnson et al. | |
| 2014/0330308 A1 | 11/2014 | Hart et al. | |
| 2014/0336635 A1 | 11/2014 | Hart et al. | |
| 2014/0353188 A1 | 12/2014 | Reschke et al. | |
| 2015/0018816 A1 | 1/2015 | Latimer | |
| 2015/0025528 A1 | 1/2015 | Arts | |
| 2015/0032106 A1 | 1/2015 | Rachlin | |
| 2015/0051598 A1 | 2/2015 | Orszulak et al. | |
| 2015/0051640 A1 | 2/2015 | Twomey et al. | |
| 2015/0066026 A1 | 3/2015 | Hart et al. | |
| 2015/0080880 A1 | 3/2015 | Sartor et al. | |
| 2015/0080889 A1 | 3/2015 | Cunningham et al. | |
| 2015/0082928 A1 | 3/2015 | Kappus et al. | |
| 2015/0088122 A1 | 3/2015 | Jensen | |
| 2015/0088126 A1 | 3/2015 | Duffin et al. | |
| 2015/0088128 A1 | 3/2015 | Couture | |
| 2015/0094714 A1 | 4/2015 | Lee et al. | |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 4211417 A1 | 10/1993 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 0589453 A2 | 3/1994 |
| EP | 1281878 A1 | 2/2003 |
| EP | 1159926 A3 | 3/2003 |
| EP | 2777586 A1 | 9/2014 |
| EP | 2890309 A1 | 7/2015 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |

(56) References Cited

FOREIGN PATENT DOCUMENTS

| | | | |
|---|---|---|---|
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/45589 | 6/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |

OTHER PUBLICATIONS

Extended European Search Report for EP 16196110 dated Dec. 23, 2016.
Michael Choti, "Abdominoperineal Resection with the LigaSure Vessel Sealing System and LigaSure Atlas 20 cm Open Instrument"; Innovations That Work, Jun. 2003. (4 pages).
Chung et al., "Clinical Experience of Sutureless Closed Hemorrhoidectomy with LigaSure" Diseases of the Colon & Rectum vol. 46, No. Jan. 1, 2003, pp. 87-92.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003. (1 page).

Peterson et al. "Comparison of Healing Process Following Ligation with Sutures and Bipolar Vessel Sealing" Surgical Technology International (2001). (8 pages).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000. (1 page).
Johnson et al. "Evaluation of the LigaSure Vessel Sealing System in Hemorrhoidectormy" American College of Surgeons (ACS) Clinicla Congress Poster (2000). (1 page).
Muller et al., "Extended Left Hemicolectomy Using the LigaSure Vessel Sealing System" Innovations That Work, Sep. 1999. (4 pages).
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002. (4 pages).
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002. (4 pages).
Koyle et al., "Laparoscopic Palomo Varicocele Ligation in Children and Adolescents" Pediatric Endosurgery & Innovative Techniques, vol. 6, No. 1, 2002, pp. 15-19.
W. Scott Helton, "LigaSure Vessel Sealing System: Revolutionary Hemostasis Product for General Surgery"; Sales/Product Literature 1999. (1 page).
LigaSure Vessel Sealing System, the Seal of Confidence in General, Gynecologic, Urologic, and Laparaoscopic Surgery; Sales/Product Literature; Apr. 2002. (8 pages).
Joseph Ortenberg "LigaSure System Used in Laparoscopic 1st and 2nd Stage Orchiopexy" Innovations That Work, Nov. 2002. (4 pages).
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001. (8 pages).
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003, pp. 147-151.
"Reducing Needlestick Injuries in the Operating Room" Sales/ Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001. (1 page).
Seyfan et al. "Sutureless Closed Hemorrhoidectomy: A New Technique" Annals of Surgery vol. 234 No. 1, Jul. 2001 pp. 21-24.

(56) References Cited

OTHER PUBLICATIONS

Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004. (1 page).
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000. (1 page).
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000. (4 pages).
Levy et al. "Use of a New Energy-based Vessel Ligation Device During Vaginal Hysterectomy" Int'l Federation of Gynecology and Obstetrics (FIGO) World Congress 1999. (1 page).
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000. (1 page).
Jarrett et al., "Use of the LigaSure Vessel Sealing System for Peri-Hilar Vessels in Laparoscopic Nephrectomy" Sales/Product Literature 2000. (1 page).
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.. (1 page).
McLellan et al. "Vessel Sealing for Hemostasis During Gynecologic Surgery" Sales/Product Literature 1999. (1 page).
U.S. Appl. No. 08/926,869, filed Sep. 10, 1997; inventor: James G. Chandler, Abandoned.
U.S. Appl. No. 09/177,950, filed Oct. 23, 1998; inventor: Randel A. Frazier, abandoned.
U.S. Appl. No. 09/387,883, filed Sep. 1, 1999; inventor: Dale F. Schmaltz, abandoned.
U.S. Appl. No. 09/591,328, filed Jun. 9, 2000; inventor: Thomas P. Ryan, abandoned.
U.S. Appl. No. 12/336,970, filed Dec. 17, 2008; inventor: Paul R. Sremeich, abandoned.
U.S. Appl. No. 14/065,644, filed Oct. 29, 2013; inventor: Reschke, abandoned.

\* cited by examiner

SURGICAL INSTRUMENTS INCLUDING CAM SURFACES

CROSS REFERENCE TO RELATED APPLICATION

The present application claims the benefit of and priority to U.S. Provisional Application Ser. No. 62/247,279, filed on Oct. 28, 2015, the entire contents of which are incorporated herein by reference.

BACKGROUND

Technical Field

The present disclosure relates to surgical instruments and, more particularly, to an endoscopic surgical forceps configured for treating and/or cutting tissue.

Background of Related Art

A surgical forceps is a pliers-like device which relies on mechanical action between its jaw members to grasp, clamp, and constrict tissue. Typically, at least one handle or lever is used to open and close the jaw members, and to provide compression force on tissue between the jaw members, to lock the jaw members in a closed position, and/or to apply energy to the jaw members to seal the tissue disposed therebetween.

Generally, such handles and levers used on surgical instruments are one of two types. One type is a simple pivoted handle that provides a near constant mechanical advantage throughout its stroke, and which is useful in many surgical situations. The second type of handle includes an additional link to provide a geometrically increasing mechanical advantage toward the end of its stroke to help provide the force necessary to compress tissue.

Both of these types of handles fix the mechanical advantage of the drive system such that the drive system cannot be optimized independently over the entire lever stroke. Often times, it may be desirable for a system to include fine dissection capability (a relatively large amount of handle travel for a relatively small amount of jaw member movement) when the jaw members are in an initial, or open position, and to include a high mechanical advantage while applying compression force to tissue disposed between the jaw members when the jaw members are in or near their approximated position (to help reduce surgeon fatigue, for instance). However, current handles are generally unable to achieve both of these desires in a single system, thus resulting in a compromised result.

SUMMARY

The present disclosure relates to a surgical instrument comprising a housing, a handle, an elongated shaft, an end effector assembly, a drive assembly, and an extension depending from the handle. The handle is pivotably connected to the housing. The elongated shaft extends distally from the housing and defines a longitudinal axis. The end effector assembly is disposed adjacent a distal end of the elongated shaft, and includes a first jaw member and a second jaw member. At least one of the jaw members is movable with respect to the other jaw member from a spaced-apart position to a position closer to one another for grasping tissue. The drive assembly is disposed at least partially within the housing and includes a drive bar extending at least partially through the elongated shaft such that longitudinal translation of the drive bar causes the jaw members to move between the spaced-apart position and the closer position for grasping tissue. The extension depends from the handle, and includes a proximal surface having a first proximal cam portion defining a first angle with respect to the longitudinal axis and a second proximal cam portion defining a second angle with respect to the longitudinal axis. Each of the first proximal cam portion and the second proximal cam portion is configured to contact a first portion of the drive assembly such that movement of the handle with respect to the housing causes longitudinal translation of the drive bar. Initial actuation of the handle from a non-actuated position causes the first proximal cam portion to contact the first portion of the drive assembly causing a first movement of the at least one jaw member, and subsequent actuation of the handle causes the second proximal cam portion to contact the first portion of the drive assembly causing a second movement of the at least one jaw member.

In disclosed embodiments, the extension includes a distal surface having a first distal cam portion defining a first angle with respect to the longitudinal axis and a second distal cam portion defining a second angle with respect to the longitudinal axis. Each of the first distal cam portion and the second distal cam portion is configured to contact a second portion of the drive assembly. It is disclosed that the first distal cam portion is configured to contact the second portion of the drive assembly while the first proximal cam portion contacts the first portion of the drive assembly. It is further disclosed that the second distal cam portion is configured to contact the second portion of the drive assembly while the second proximal cam portion contacts the first portion of the drive assembly.

Additionally, it is disclosed that the first portion of the drive assembly is a follower, the second portion of the drive assembly is a pin, and the pin is biased proximally into contact with the distal surface. In disclosed aspects, the pin is longitudinally translatable with resect to the housing. In further disclosed aspects, the follower is longitudinally translatable with resect to the housing. It is also disclosed that the surgical instrument comprises a conical spring configured to bias the pin into contact with the distal surface.

In disclosed embodiments, the proximal surface includes a divot configured to engage the first portion of the drive assembly to help maintain the longitudinal position of the drive bar. It is further disclosed that the divot is configured to engage the first portion of the drive assembly when the handle is in a fully approximated position.

The present disclosure also relates to methods of performing a surgical procedure. Disclosed methods include moving a handle of a surgical instrument from a non-actuated position a first distance to an intermediate position to cause a first jaw member of the surgical instrument to move a first amount, and moving the handle of the surgical instrument from the intermediate position a second distance to a fully actuated position to cause the first jaw member of the surgical instrument to move a second amount. The first distance is the same as the second distance, and the first amount is less than the second amount.

In disclosed embodiments, moving the handle of the surgical instrument from the non-actuated position to the intermediate position includes engaging a first proximal cam portion of an extension depending from the handle to with a first portion of a drive assembly of the surgical instrument. It is further disclosed that moving the handle of the surgical instrument from the intermediate position to the fully actuated position includes engaging a second proximal cam portion of the extension with the first portion of a drive assembly of the surgical instrument.

Further embodiments of disclosed methods include longitudinally translating the first portion of the drive assembly with respect to a housing of the surgical instrument, and/or engaging a divot disposed on a proximal surface of the extension with the first portion of the drive assembly.

BRIEF DESCRIPTION OF THE DRAWINGS

Various aspects and features of the present disclosure described herein with reference to the drawings wherein.

DETAILED DESCRIPTION

Figure 1:
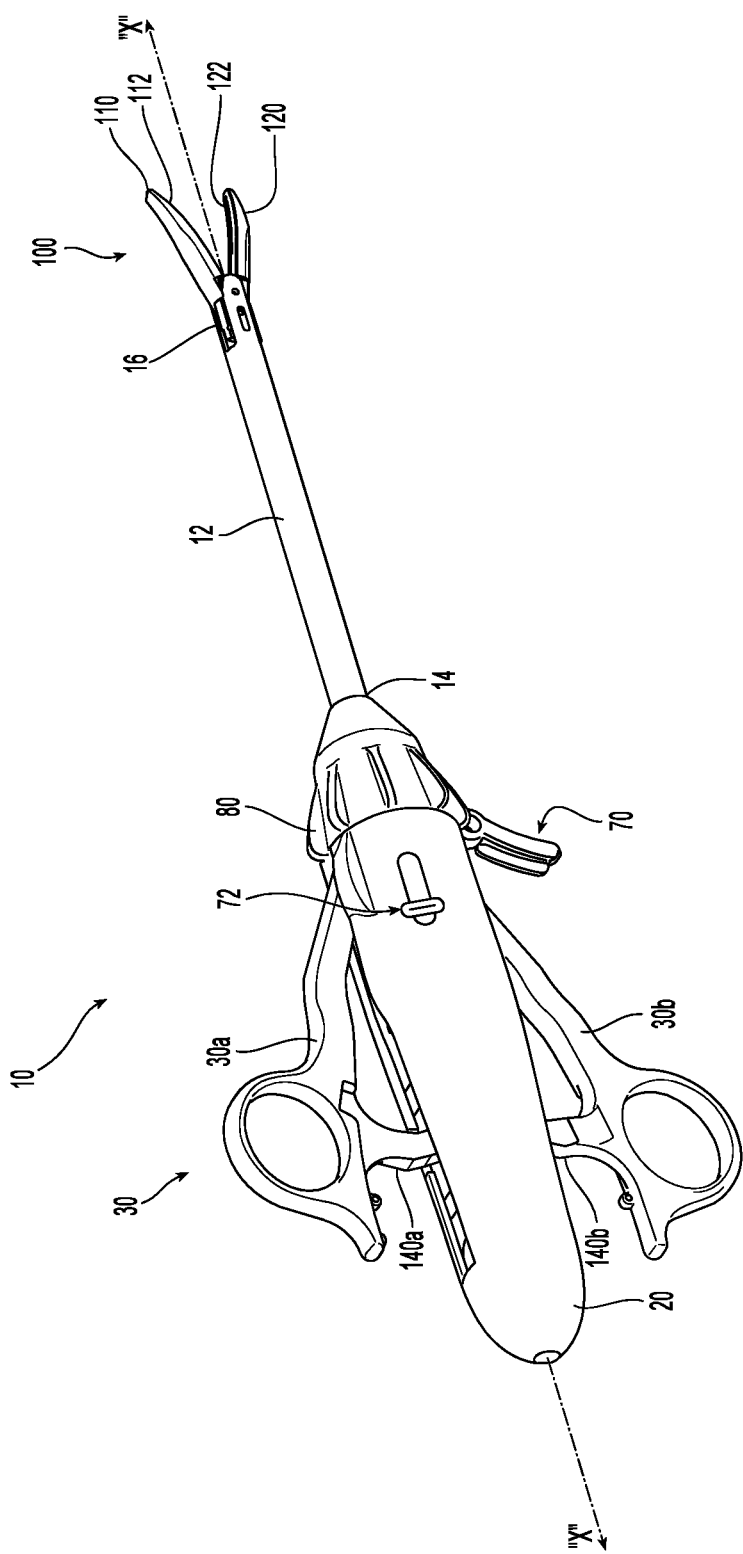
FIG. 1 is a perspective view of a surgical forceps provided in accordance with the present disclosure.

Embodiments of the presently disclosed surgical forceps are described in detail with reference to the drawings, in which like reference numerals designate identical or corresponding elements in each of the several views. As used herein the term "distal" refers to that portion of the surgical forceps that is farther from the user, while the term "proximal" refers to that portion of the surgical forceps that is closer to the user.

With initial reference to FIG. 1, an embodiment of a surgical forceps in accordance with the present disclosure is shown generally identified by reference numeral 10. Although surgical forceps 10 is shown configured for use in connection with endoscopic surgical procedures, the present disclosure is equally applicable for surgical instruments used in open surgical procedures and in connection with any suitable surgical instrument. For the purposes herein, forceps 10 is generally described.

Forceps 10 is adapted for use in various surgical procedures and generally includes a housing 20, a handle assembly 30, a trigger assembly 70, a rotating assembly 80, and an end effector assembly 100. Jaw members 110 and 120 of end effector assembly 100 mutually cooperate to grasp, treat, seal and/or cut tissue. Forceps 10 further includes a shaft 12 having a distal end 16 that mechanically engages end effector assembly 100 and a proximal end 14 that mechanically engages housing 20. Forceps 10 may be configured to connect to a source of energy, e.g., a generator (not shown), forceps 10 may be configured as a battery powered instrument, or forceps 10 may be manually powered (e.g., when providing electrosurgical energy is not desired).

Handle assembly 30 includes a first movable handle 30a and a second movable 30b disposed on opposite sides of housing 20. Handles 30a and 30b are movable relative to one another to actuate end effector assembly 100, as will be described in greater detail below. Further, while two movable handles 30a and 30b are shown and described herein, the present disclosure also includes handle assembly 30 including a single movable handle. Here, in addition to the single movable handle, a finger loop may be included on the opposite side of housing 20 as the single movable handle.

Rotating assembly 80 is mechanically coupled to housing 20 and is rotatable in either direction, to rotate shaft 12 and, thus, end effector assembly 100 about a longitudinal axis "X" defined by shaft 12. Such a configuration allows end effector assembly 100 to be rotated in either direction with respect to housing 20.

Figure 2:
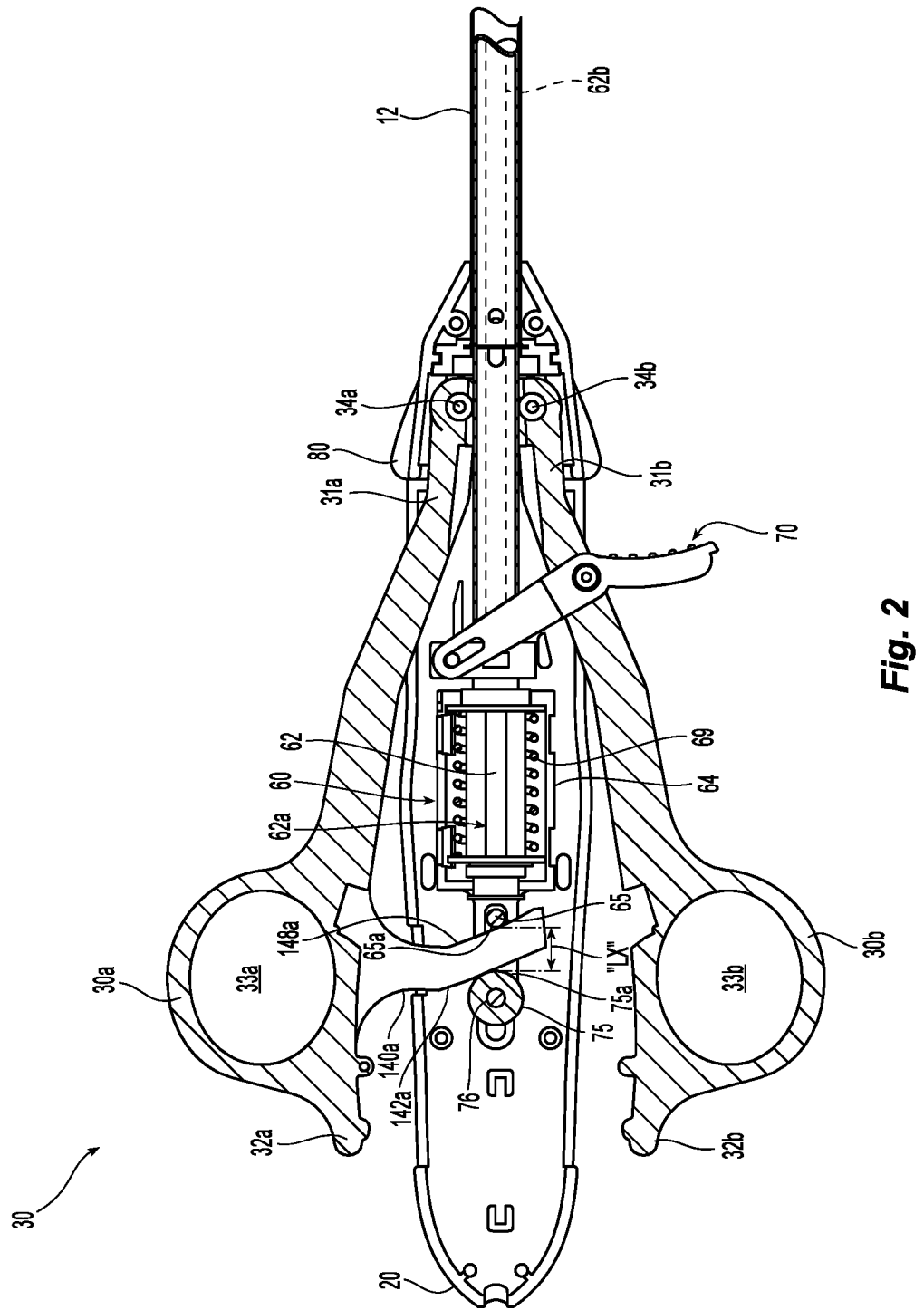
FIG. 2 is a sectional view of a handle assembly of the surgical forceps of FIG. 1 where a first cam of a first handle is shown, and where a second cam of a second handle is omitted.
Figure 3:
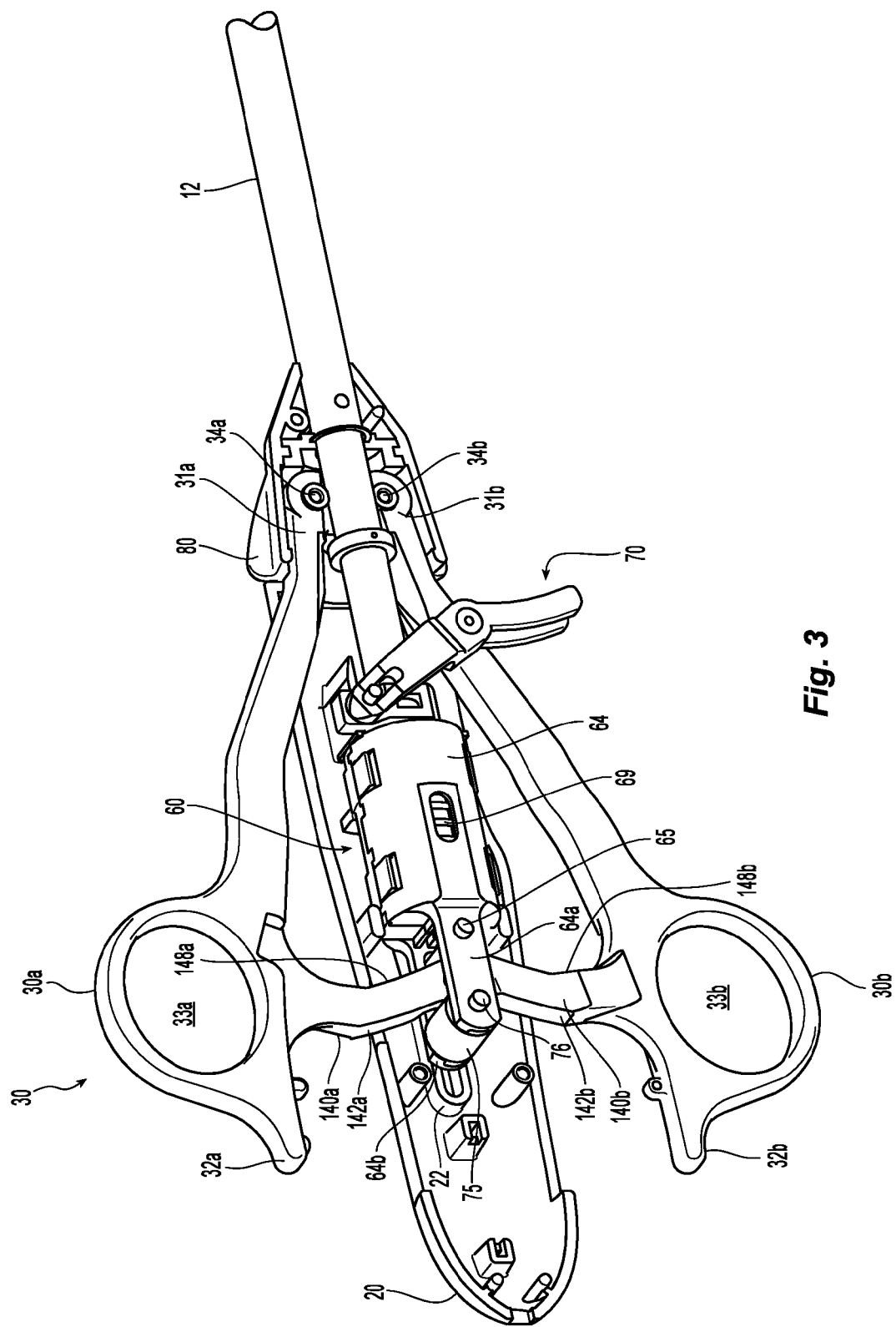
FIG. 3 is a perspective view of internal components of the handle assembly of FIG. 1.

With reference to FIGS. 2 and 3, handles 30a and 30b of handle assembly 30 ultimately connect to a drive assembly 60 disposed within housing 20 and extending through shaft 12 which, together, cooperate to impart movement of jaw members 110 and 120 from an open position wherein jaw members 110 and 120 are disposed in spaced relation relative to one another, to a closed or approximated position wherein jaw members 110 and 120 cooperate to grasp tissue therebetween.

Handles 30a and 30b of handle assembly 30 each include an aperture 33a and 33b, respectively, defined therein which enables a user to grasp and move handles 30a and 30b relative to one another and housing 20 between a spaced-apart position and an approximated position. Handles 30a and 30b are pivotably coupled to housing 20 at their respective distal ends 31a, 31b via pivot pins 34a, 34b, respectively, and extend proximally to proximal ends 32a, 32b, respectively, thereof. As mentioned above, handles 30a, 30b are coupled to drive assembly 60 such that pivoting of handles 30a, 30b about pivot pins 34a, 34b, respectively, and relative to one another effects pivoting of jaw members 110, 120 between the open and closed positions, as discussed in further detail below.

With particular reference to FIGS. 2, 3, 5 and 6, drive assembly 60 includes a drive bar 62 defining a proximal end 62a disposed within housing 20 and a distal end 62b that extends through shaft 12, ultimately coupling to jaw members 110, 120. A mandrel 64 disposed within housing 20 is engaged with the proximal end 62a of drive bar 62. Mandrel 64 is slidably engaged with at least one track 22 (see FIGS. 3, 5 and 6) defined within housing 20 to guide longitudinal translation of mandrel 64 and, thus, drive bar 62, relative to housing 20. Other suitable guide/alignment mechanisms are also contemplated. A spring 69 is positioned within mandrel 64 and is configured to bias drive bar 62 distally, thereby biasing jaw members 110, 120, towards the open position.

A follower 75 is rotatably supported by an axle 76, which extends through a bore of follower 75. Axle 76 is supported (e.g., rotatably supported) by proximal extensions 64a, 64b of mandrel 64. A cam follower (e.g., a pin within a sleeve) 65 is also supported (e.g., rotatably supported) by proximal extensions 64a, 64b of mandrel 64.

In order to move jaw members 110, 120 from the open position to the closed position, handles 30a, 30b are squeezed, e.g., pivoted about pivot pins 34a, 34b, inwardly towards one another and housing 20. As handles 30a, 30b are pivoted in this manner, proximal ends 32a, 32b of handles 30a, 30b are approximated relative to housing 20 and one another. The approximation of proximal ends 32a, 32b of handles 30a, 30b towards one another causes extensions 140a, 140b of respective handles 30a, 30b to urge follower 75, mandrel 64 and drive bar 62 proximally, thus approximating jaw members 110, 120. Movement of handles 30a, 30b toward their open position causes extensions 140a, 140b to urge cam follower 65, mandrel 64 and drive bar 62 distally, thus causing jaw members 110, 120 to move toward their open position, as further described below. The spring force of spring 69 may be configured such that jaw members 110, 120 impart a closure force between jaws within a range of about 3 kg/cm$^2$ to about 16 kg/cm$^2$, although other closure forces are also contemplated.

During use, it is often desired to have fine (vs. gross) control of jaw members 110, 120 during some stages of use. For example, a surgeon may wish to have great control of movement of the jaw members 110, 120 during dissection of tissue, manipulation of tissue, and precise placement of jaw members 110, 120 about target tissue. For such fine control of jaw members 110, 120, a relative large amount of travel of handles 30a, 30b (or a single handle) would correspond to a relative small amount of travel of jaw members 110, 120. Some surgeons may also desire to have a high mechanical advantage during other stages of use. For example, a surgeon may wish to utilize a high mechanical advantage while applying compression force to tissue. To achieve such a high mechanical advantage, a relative small amount of travel of handles 30a, 30b would correspond to a relative large amount of travel of jaw members 110, 120. Typically, surgical instruments only allow for either fine control of jaw members 110, 120 or a high mechanical advantage.

Surgical forceps 10 of the present disclosure allows for both fine control of jaw members 110, 120 and a high mechanical advantage at different stages of the actuation stroke of handles 30a, 30b. Specifically, each extension 140a, 140b includes a respective proximal cam surface 142a, 142b and a respective distal cam surface 148a, 148b. Proximal cam surfaces 142a, 142b are configured to contact follower 75 along the entire actuation stroke of handles 30a, 30b, and distal cam surfaces 148a, 148b are configured to contact cam follower 65 along the entire actuation stroke of handles 30a, 30b.

Figure 4:
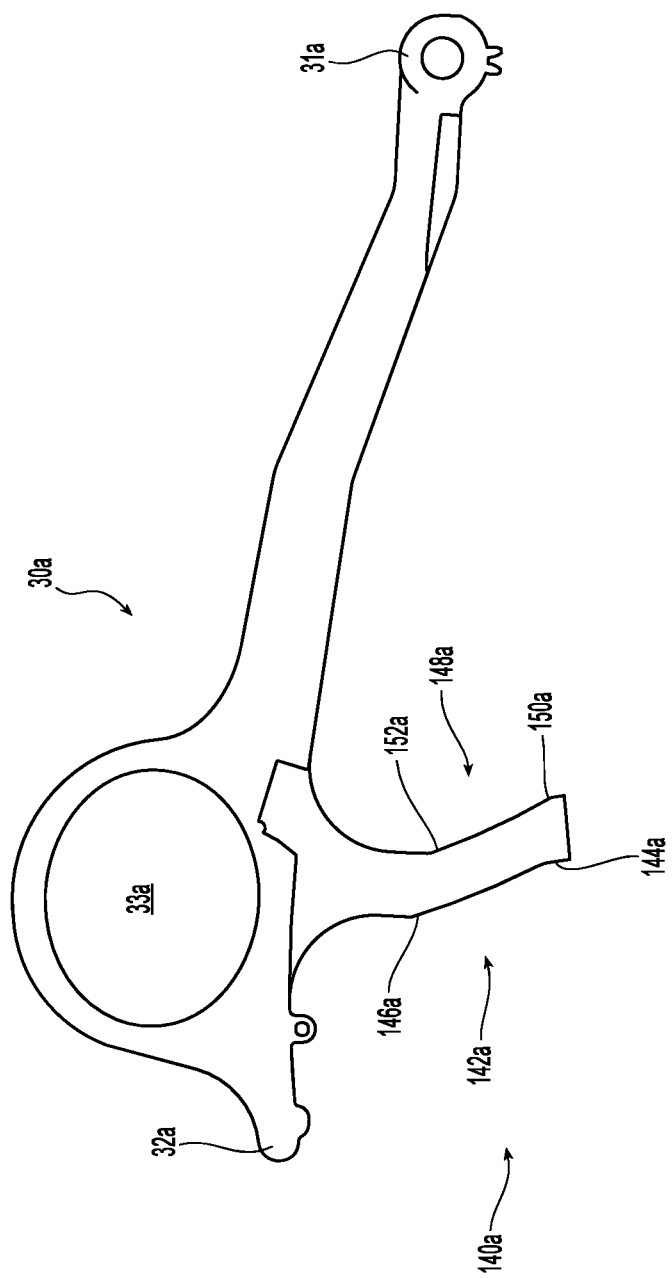
FIG. 4 is a side view of the first handle and the first extension of the handle assembly of FIGS. 2 and 3.

With particular reference to FIG. 4, where only a single handle 30a is shown, proximal cam surface 142a includes a first portion 144a and a second portion 146a, and distal cam surface 148a includes a first portion 150a and a second portion 152a. Engagement between first portions 144a and 150a and follower 75 and cam follower 65, respectively, causes each jaw member 110, 120 to move a first distance, and engagement between second portions 146a, 152a and follower 75 and cam follower 65, respectively, causes each jaw member 110, 120 to move a second distance.

As can be appreciated, the precise cam profiles of proximal cam surface 142a and distal cam surface 148a can be configured to provide a particular amount (e.g., a fine amount) of control of jaw members 110, 120 at the beginning of an actuation stroke (i.e., when first portions 144a, 150a contact follower 75 and cam follower 65, respectively) and a particular amount (e.g., a gross amount) of control at the end of an actuation stroke (i.e., when second portions 146a, 152a contact follower 75 and cam follower 65, respectively).

More particularly, in disclosed embodiments, proximal cam surface 142a and distal cam surface 148a are each configured such that when handle 30a is initially actuated a first distance (i.e., from a fully-open position), less movement of jaw members 110, 120 occurs than when handle 30a is subsequently actuated the same distance. As such, jaw members 110, 120 are more finely controlled during the initial actuation of handle 30a (or handles 30a, 30b). Additionally, movement of handle 30a toward its fully open position results in movement of jaw members 110, 120 toward their open positions. As can be appreciated, the precise curvature of proximal cam surface 142a and distal cam surface 148a can be varied based on particular requirements or surgeon preferences. For instance, first portions 144a, 150a can have a smaller or larger slope (or slopes) than what is illustrated, and second portions 146a, 152a can similarly have a smaller or larger slope (or slopes) than what is illustrated.

Figure 4A:
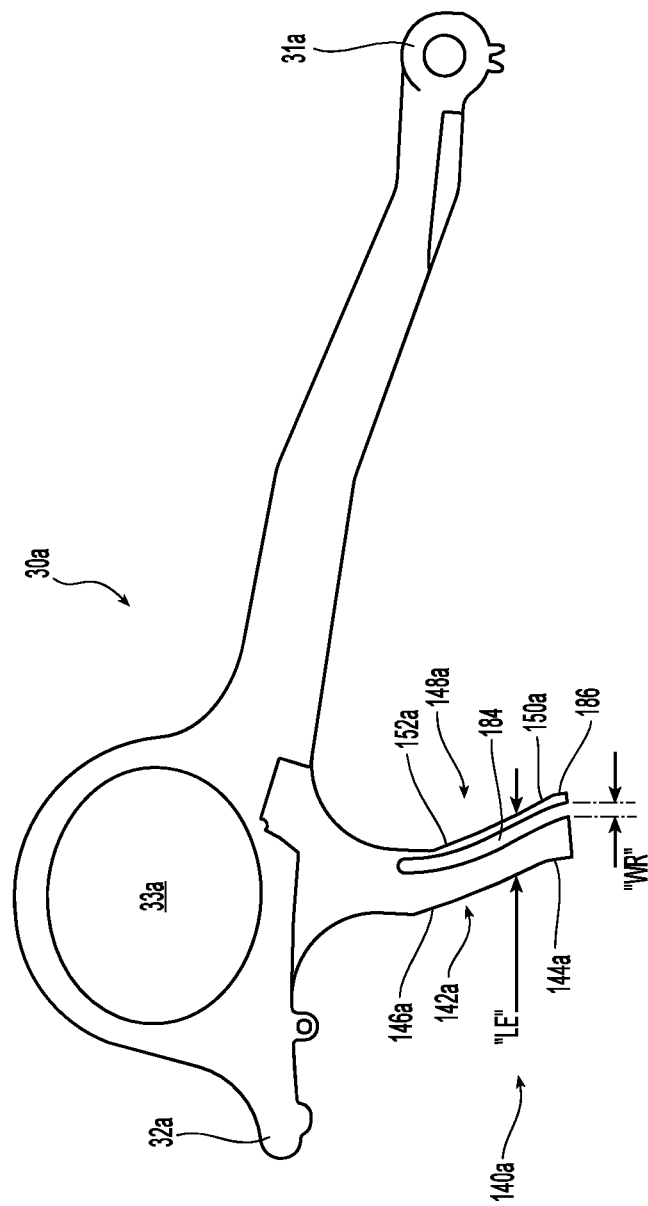
FIG. 4A is a side view of a first handle in accordance with an alternate embodiment of the present disclosure.
Figure 4B:
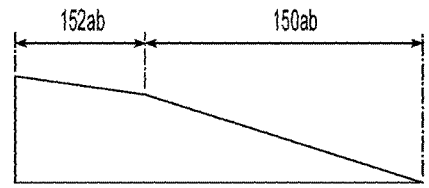
FIGS. 4B-4G are schematic examples of different cam profiles for use with at least one extension of a handle according to embodiments of the present disclosure.
Figure 4C:
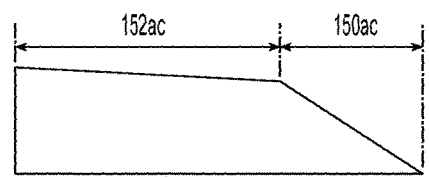
Figure 4D:
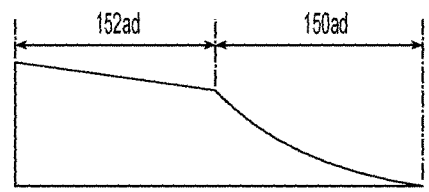
Figure 4E:
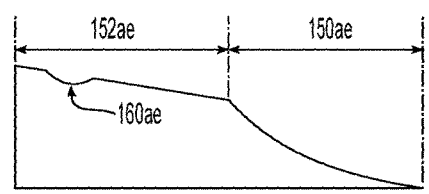
Figure 4F:
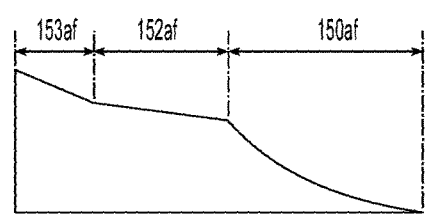
Figure 4G:
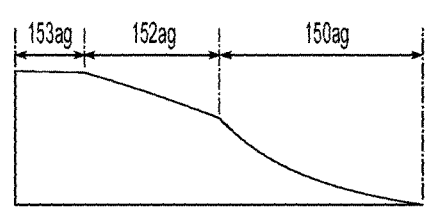

FIGS. 4B-4G illustrate different cam profiles that can be utilized on extension 140 (e.g., 140a and/or 140b). More particularly, while each cam profile (or a corresponding cam profile) can be used on either proximal cam surface 142a and/or distal cam surface 148a, the following discussion is in relation to the particular cam profile being included on distal cam surface 148a. In FIG. 4B, first portion 150ab is longer than and includes a moderately steeper slope than second portion 152ab, which results in relatively slowly closing the jaw members 110, 120 (corresponding to first portion 150ab), and relatively minimal force required for tissue compression (corresponding to second portion 152ab). In FIG. 4C, first portion 150ac is shorter than and includes a steeper slope than second portion 152ac, which results in relatively quickly closing the jaw members 110, 120 (corresponding to first portion 150ac), and less force required for tissue compression (corresponding to second portion 152ac) relative to second portion 152ab in the embodiment shown in FIG. 4B. In FIG. 4D, first portion 150ad is about the same length as second portion 152ad, and first portion 150ad includes an arcuate slope while second portion 152ad includes a linear slope. The arcuate slope of the first portion 150ad helps compensate for jaw slot non-linearity, which results in an approximate linear relationship between handle movement and jaw closure. The cam profile in FIG. 4E includes a first portion 150ae and a second portion 152ae, and is similar to the cam profile in FIG. 4D, but also includes a locking portion 160ae, which, when engaged with cam follower 65, maintains the extension 140 in position when the jaw members 110, 120 are closed and tissue is compressed therebetween, for example. The cam profile in FIG. 4F includes a first portions 150af and a second portion 152af, and is similar to the cam profile in FIG. 4E, but instead of locking portion 160ae, a force feedback section 153af is included. Force feedback section 153af has a relatively steep slope such that when engaged by cam follower 65, the level of force dramatically increases after tissue is sufficiently compressed, thus indicating to the user that the tissue is ready to be sealed. The cam profile in FIG. 4G, includes a first portion 150ag and a second portion 152ag, which are similar to the respective first and second portions 150af, 152af of the cam profiles in FIG. 4F, and also includes an easy hold portion 153ag. Each hold portion 153ag enables the jaw members 110, 120 to remain in the approximated position with little mechanical effector from the user (e.g., surgeon).

The cam profiles shown in FIGS. 4B-4G are only examples of different types of cam profiles that can be included on extensions 140a and/or 140b, as other cam profiles not specifically shown are also usable for similarly effecting the movement of jaw members 110, 120.

Additionally, the present disclosure includes a surgical kit including surgical forceps 10 with multiple extensions 140. Extensions 140 may be removable and engageable with handle(s) 30a, 30b by suitable mechanical structure (e.g., a snap-fit connection). Extensions 140 of such a surgical kit include different cam profiles, such that a physician can opt to use a particular extension 140 based on personal preferences or the particular procedure being performed.

Handle 30*b* may include the same, mirror-image, or corresponding proximal and distal cam surfaces as handle 30*a*.

Figure 5:
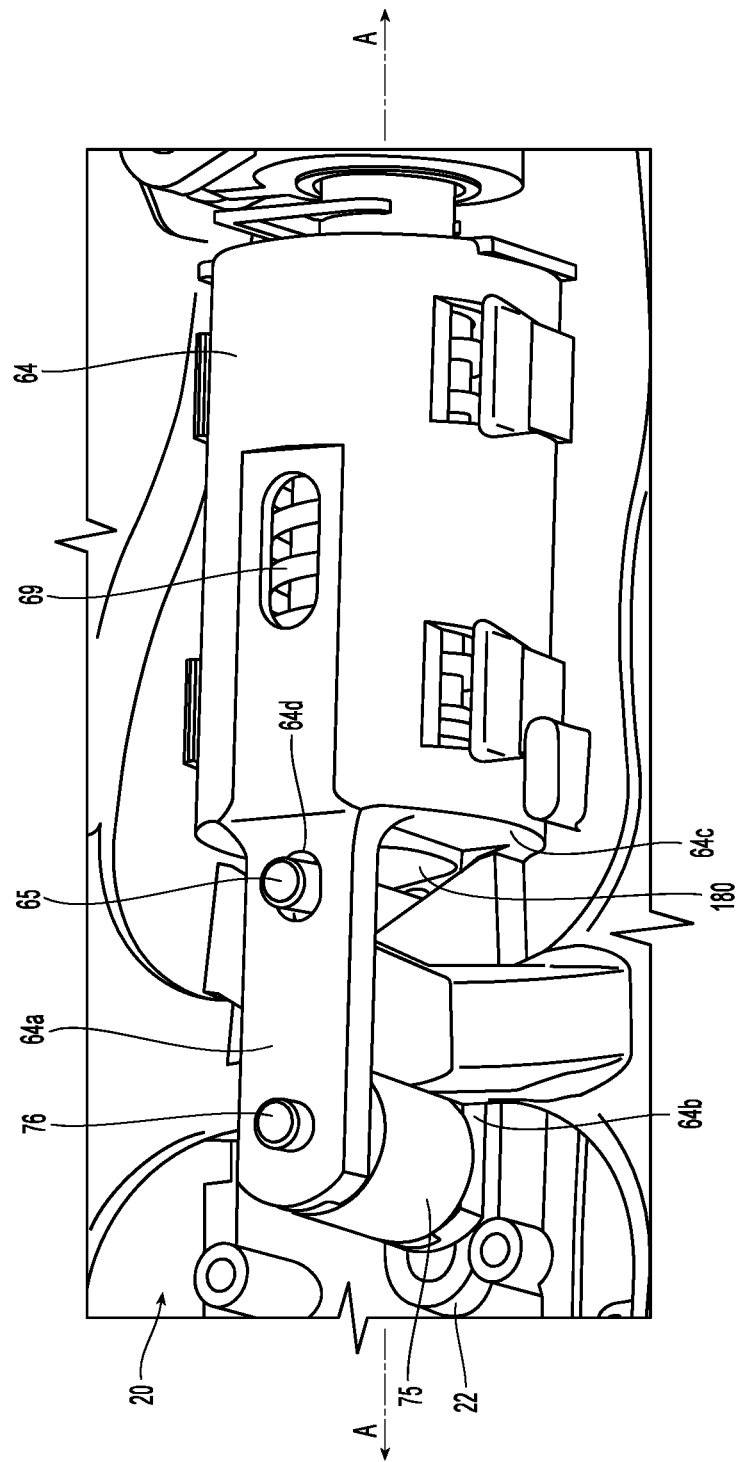
FIG. 5 is a perspective view of an alternate embodiment of portions of the handle assembly.

Additionally, and with particular reference to FIGS. 2, 3 and 5, follower 75 is configured to maintain contact with proximal cam surfaces 142*a*, 142*b* throughout the actuation stroke of handles 30*a*, 30*b*.

To help ensure that contact is maintained between follower 75 and proximal cam surfaces 142*a*, 142*b*, and between cam follower 65 and distal cam surfaces 148*a*, 148*b* (e.g., to account for manufacturing tolerances, and/or to allow greater manufacturing tolerances, thus reducing costs), surgical forceps 10 may include an engagement spring 180 disposed between a proximal wall 64*c* of mandrel 64 and cam follower 65. Engagement spring 180 is configured to urge cam follower 65 proximally toward and into contact with distal cam surfaces 148*a*, 148*b*. Here, cam follower 65 is slidably supported by slots 64*d* in proximal extensions 64*a*, 64*b* of mandrel 64 (see FIG. 5). Engagement spring 180 may be cone-like (e.g., frusto-conical) in shape, or a Belleville washer.

With particular reference to FIG. 4A, an additional way of ensuring contact is maintained between follower 75 and proximal cam surfaces 142*a*, 142*b*, and between cam follower 65 and distal cam surfaces 148*a*, 148*b* (and thus reducing or removing free play therebetween) is the inclusion of a relief 184 within extension 140*a* of handle 30*a*. While FIG. 4A only illustrates handle 30*a*, it is within the scope of the present disclosure to include a similar relief in handle 30*b*. As shown in FIG. 4A, the inclusion of relief 184 creates a lever spring 186 on a distal portion of extension 140*a*. Handles 30*a*, 30*b* including relief 184 may be configured to be used when a longitudinal length "LE" of extensions 140*a*, 140*b* (FIG. 4A) is larger than the longitudinal distance "LX" (FIG. 2) between a proximal surface 65*a* of cam follower 65 and a distal surface 75*a* of follower 75. Here, a width "WR" of relief 184 would shorten, and would thus pre-load lever spring 186. Accordingly, the inclusion of relief 184 and lever spring 186 would fill any gap between cam follower 65 and follower 75, thus reducing or removing any free play (i.e., unimpeded longitudinal movement) of extensions 140*a*, 140*b*.

Figure 6:
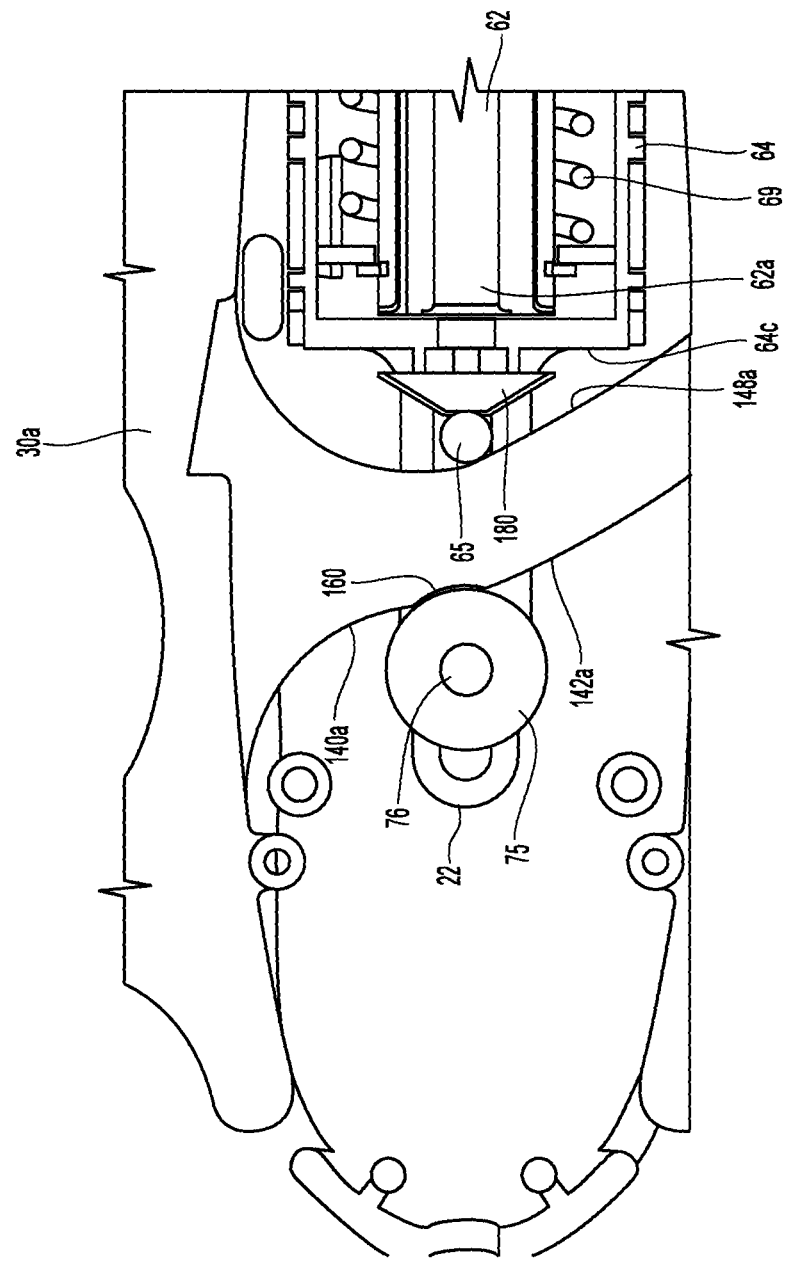
FIG. 6 is a cross-sectional view of the portions of the handle assembly of FIG. 5 taken along line A-A.

Referring now to FIG. 6, the present disclosure also includes embodiments where proximal cam surfaces 142*a*, 142*b* of respective extensions 140*a*, 140*b* of each handle 30*a*, 30*b* include an arcuate divot 160. In FIG. 6, only divot 160 in connection with handle 30*a* is illustrated; either or both handles 30*a*, 30*b* may include divot 160. The shape of divot 160 corresponds to the outer curvature of follower 75. Divot 160 is positioned such that follower 75 engages divot 160 when the respective handle(s) 30*a*, 30*b* are in their fully closed position, which corresponds to jaw members 110, 120 being in their fully approximated position (e.g., with a predetermined gap therebetween). The engagement between follower 75 and divot 160 helps maintain handle(s) 30*a*, 30*b* in the closed position.

Feedback may be provided to the user when follower 75 engages divot 160. Such a feature is useful when a user desires to initiate tissue sealing (e.g., by actuation of trigger assembly 70) after jaw members 110, 120 are fully approximated. The feedback can be provided by the way of tactile feedback (e.g., a tactile click) or audible feedback (e.g., an audible click), for instance.

With tissue grasped between jaw members 110, 120, energy may be supplied to tissue-contacting surfaces 112, 122 and conducted through tissue to treat, e.g., seal, tissue via activation of a switch 72 disposed on housing 20. While switch 72 is shown as being longitudinally-translatable, it is also disclosed that switch 72 is lever-actuated or pivotable. Trigger assembly 70 is actuated to advance a knife blade (not explicitly shown) between jaw members 110, 120 to cut the tissue grasped therebetween. Thereafter, release or return of handles 30*a*, 30*b* to the spaced-apart position relative to one another and housing 20 causes distal movement of mandrel 64 and drive bar 62, and causes jaw members 110, 120 to be moved back to the open position to release the treated and/or cut tissue.

Additionally, while the illustrated embodiments depict one type of surgical device 10, the present disclosure includes the use of various features described herein (e.g., proximal and/or distal cam surfaces contacting a follower and/or a pin) in connection with other types of surgical devices including at least one pivotable handle or lever. For instance, various handle assemblies for actuating handle(s) and corresponding drive assemblies are contemplated for translating drive bar 62 and are discussed in commonly-owned U.S. Pat. No. 7,857,812, the entire contents of which are incorporated by reference herein.

Additionally, further details of a surgical forceps having a similar handle assembly to the disclosed handle assembly 30 are disclosed in U.S. Pat. No. 8,430,876, the entire contents of which being incorporated by reference herein. Further details of an electrosurgical instrument are disclosed in U.S. Pat. Nos. 7,101,371 and 7,083,618, the entire contents of which being incorporated by reference herein.

The present disclosure also includes methods of manipulating jaw members 110, 120 using fine and gross controls, and described above. For example, disclosed methods include moving handle 30*a*, 30*b* of surgical instrument 10 from a non-actuated position a first distance to an intermediate position to cause first jaw member 110 to move a first amount, and moving handle 30*a*, 30*b* from the intermediate position a second distance to a fully actuated position to cause first jaw member 110 to move a second amount. Here, the first distance is the same as the second distance, and the first amount is less than the second amount, thus resulting in an initial fine movement of jaw member 110, and a subsequent gross movement of jaw member 110.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prepare the patient for surgery and configure the robotic surgical system with one or more of the surgical instruments disclosed herein while another surgeon (or group of surgeons) remotely controls the instrument(s) via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 7:
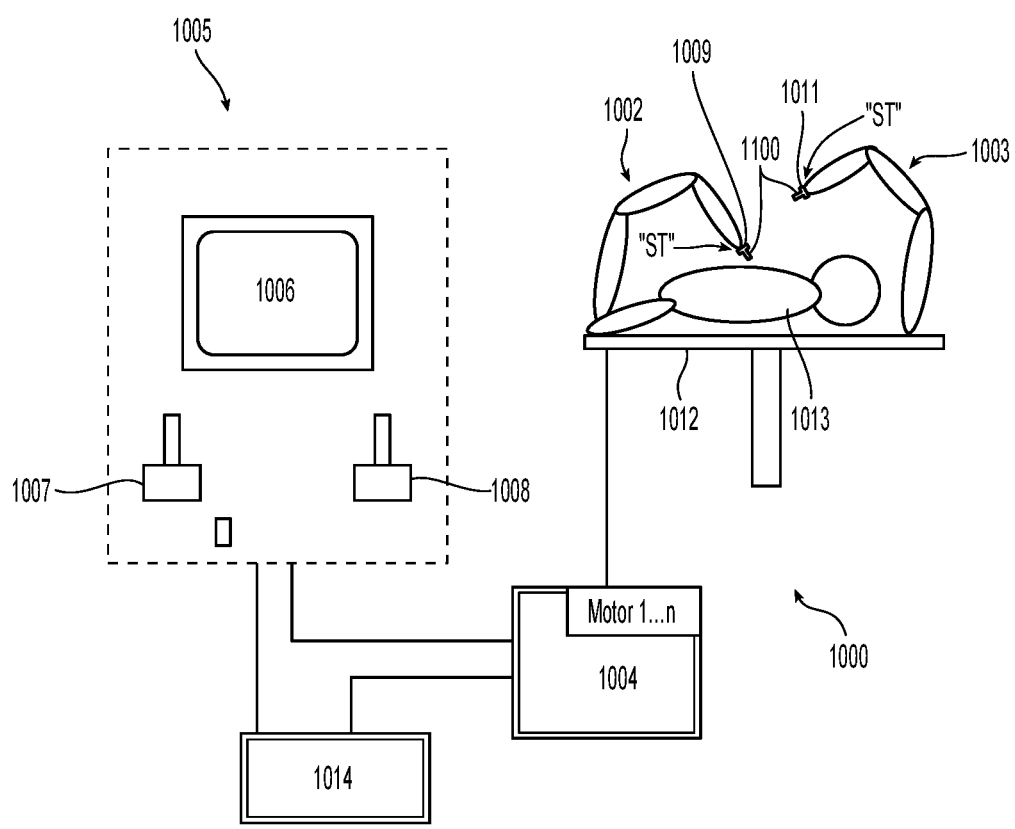
FIG. 7 is a schematic illustration of a surgical system in accordance with the present disclosure.

With particular reference to FIG. 7, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus surgical instrument 10 (including end effector 300) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
a housing;
a handle pivotably connected to the housing;
an elongated shaft extending distally from the housing and defining a longitudinal axis;
an end effector assembly disposed adjacent a distal end of the elongated shaft, the end effector assembly including a first jaw member and a second jaw member, at least one of the jaw members being movable with respect to the other jaw member from a spaced-apart position to a position closer to one another for grasping tissue;
a drive assembly disposed at least partially within the housing, the drive assembly including a drive bar extending at least partially through the elongated shaft such that longitudinal translation of the drive bar causes the jaw members to move between the spaced-apart position and the closer position for grasping tissue; and
an extension connected to and extending from the handle, wherein the extension includes a proximal surface having a first proximal cam portion defining a first angle with respect to the longitudinal axis and a second proximal cam portion defining a second angle with respect to the longitudinal axis, each of the first proximal cam portion and the second proximal cam portion configured to contact a first portion of the drive assembly such that movement of the handle with respect to the housing causes longitudinal translation of the drive bar, wherein a distal surface of the first portion of the drive assembly is rounded, wherein initial actuation of the handle from a non-actuated position causes the first proximal cam portion to contact the first portion of the drive assembly causing a first movement of the at least one jaw member, and wherein subsequent actuation of the handle causes the second proximal cam portion to contact the first portion of the drive assembly causing a second movement of the at least one jaw member.

2. The surgical instrument according to claim 1, wherein the extension includes a distal surface having a first distal cam portion defining a first angle with respect to the longitudinal axis and a second distal cam portion defining a second angle with respect to the longitudinal axis, each of the first distal cam portion and the second distal cam portion is configured to contact a second portion of the drive assembly.

3. The surgical instrument according to claim 2, wherein the first distal cam portion is configured to contact the second portion of the drive assembly while the first proximal cam portion contacts the first portion of the drive assembly.

4. The surgical instrument according to claim 3, wherein the second distal cam portion is configured to contact the second portion of the drive assembly while the second proximal cam portion contacts the first portion of the drive assembly.

5. The surgical instrument according to claim 2, wherein the first portion of the drive assembly is a follower, wherein the second portion of the drive assembly is a cam follower, and wherein the cam follower is biased proximally into contact with the distal surface.

6. The surgical instrument according to claim 5, wherein the cam follower is longitudinally translatable with respect to the housing.

7. The surgical instrument according to claim 5, wherein the follower is longitudinally translatable with respect to the housing.

8. The surgical instrument according to claim 5, further comprising a conical spring configured to bias the cam follower into contact with the distal surface.

9. The surgical instrument according to claim 1, wherein the proximal surface includes a divot configured to engage the first portion of the drive assembly to help maintain the longitudinal position of the drive bar.

10. The surgical instrument according to claim 9, wherein the divot is configured to engage the first portion of the drive assembly when the handle is in a fully approximated position.

11. The surgical instrument according to claim 1, wherein the first portion of the drive assembly is rotatable relative to the extension.

12. A method of performing a surgical procedure, comprising:
moving a handle of a surgical instrument from a non-actuated position a first distance to an intermediate position such that a first proximal cam portion of an extension of the handle engages a rounded surface of a first portion of a drive assembly of the surgical instrument to cause a first jaw member of the surgical instrument to move a first amount; and
moving the handle of the surgical instrument from the intermediate position a second distance to a fully actuated position to cause the first jaw member of the surgical instrument to move a second amount;
wherein the first distance is the same as the second distance, and wherein the first amount is less than the second amount.

13. The method according to claim 12, wherein moving the handle of the surgical instrument from the intermediate position to the fully actuated position includes engaging a second proximal cam portion of the extension with the first portion of a drive assembly of the surgical instrument.

14. The method according to claim 12, further comprising longitudinally translating the first portion of the drive assembly with respect to a housing of the surgical instrument.

15. The method according to claim 12, further comprising engaging a divot disposed on a proximal surface of the extension with the first portion of the drive assembly.

16. The method according to claim 12, further comprising rotating the first portion of the drive assembly relative to the extension of the handle.

* * * * *